United States Patent
Chapin

(10) Patent No.: US 9,907,573 B2
(45) Date of Patent: Mar. 6, 2018

(54) SKIN-CARE APPARATUS

(71) Applicant: Chapin Enterprises LLC, West Henrietta, NY (US)

(72) Inventor: John Chapin, West Henrietta, NY (US)

(73) Assignee: Beautiful—Bod LLC, Henrietta, NY (US)

( * ) Notice: Subject to any disclaimer, the term of this patent is extended or adjusted under 35 U.S.C. 154(b) by 604 days.

(21) Appl. No.: 14/492,346

(22) Filed: Sep. 22, 2014

(65) Prior Publication Data

US 2015/0088162 A1 Mar. 26, 2015

Related U.S. Application Data

(60) Provisional application No. 61/881,577, filed on Sep. 24, 2013.

(51) Int. Cl.
| | |
|---|---|
| A61B 17/54 | (2006.01) |
| A45D 34/04 | (2006.01) |
| A45D 44/22 | (2006.01) |
| A45D 34/00 | (2006.01) |

(52) U.S. Cl.
CPC .............. *A61B 17/54* (2013.01); *A45D 34/04* (2013.01); *A45D 44/22* (2013.01); *A45D 2034/007* (2013.01); *A45D 2200/1018* (2013.01); *A45D 2200/1054* (2013.01)

(58) Field of Classification Search
CPC ......... A61B 17/54; A45D 34/04; A45D 44/22
USPC .................................................. 606/131, 235
See application file for complete search history.

(56) References Cited

U.S. PATENT DOCUMENTS

| | | | |
|---|---|---|---|
| 4,892,091 A | 1/1990 | Sullenger | |
| 5,628,083 A * | 5/1997 | Hayes | A47K 7/024 15/210.1 |
| 5,730,709 A | 3/1998 | Sergent | |

(Continued)

FOREIGN PATENT DOCUMENTS

WO    WO9943249 A1    9/1999

OTHER PUBLICATIONS

Castscratcher, "The Original Catscratcher" product sheet found at castscratcher.com and https://www.facebook.com/castscratcher; published online Jan. 13, 2011, retrieved Feb. 12, 2013, total 9 pages.

*Primary Examiner* — Vy Bui
(74) *Attorney, Agent, or Firm* — Barclay Damon LLP

(57) ABSTRACT

A hand-held skin-treatment apparatus includes a deformable cover enclosing a longitudinally-extending volume. The cover has an exterior surface with a selected surface roughness. An elongated rigid support member is arranged within the volume. A compliant member is disposed within the volume and at least partly between the support member and the cover, so that the cover is held substantially stationary with respect to the compliant member. Another apparatus includes an elongated flexible support member. A tip protrudes transversely from a distal end of the support member and a handle is attached to the proximal end. An elongated compliant member is attached to the support member along the length of the compliant member. A cover encloses the tip, part of the compliant member, and a corresponding part of the support member, and has lower surface roughness over a dorsal side than over a ventral side of the support.

20 Claims, 8 Drawing Sheets

(56) References Cited

U.S. PATENT DOCUMENTS

| | | | | |
|---|---|---|---|---|
| 6,006,761 | A * | 12/1999 | Meledandri | A45D 33/34 132/317 |
| 6,835,019 | B2 * | 12/2004 | White | A45D 34/042 401/174 |
| 7,661,897 | B1 * | 2/2010 | Jackson | A45D 34/04 401/183 |
| 2007/0098768 | A1 | 5/2007 | Close et al. | |
| 2008/0115302 | A1 | 5/2008 | Kilkenny et al. | |
| 2010/0242201 | A1 | 9/2010 | Linzell | |
| 2011/0197917 | A1 | 8/2011 | Koptis et al. | |
| 2012/0259362 | A1 * | 10/2012 | Weinland | A41D 13/087 606/235 |

* cited by examiner

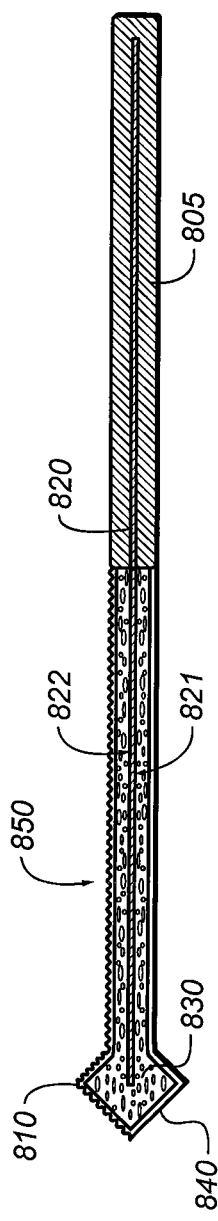
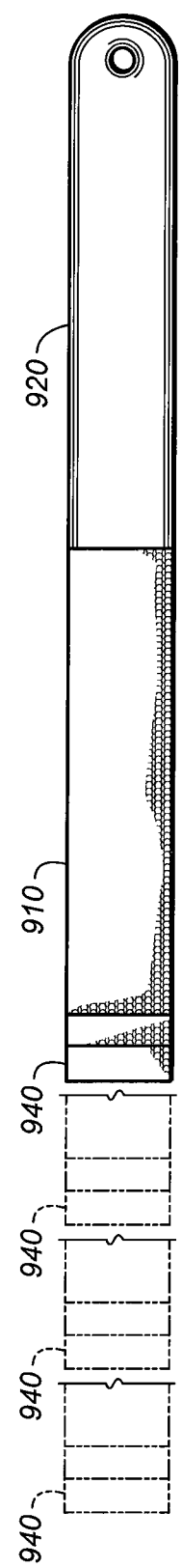

SKIN-CARE APPARATUS

CROSS-REFERENCE TO RELATED APPLICATIONS

This application claims the benefit of the filing date of U.S. Provisional Application Ser. No. 61/881,577 filed Sep. 24, 2013, the specification of which is incorporated wherein by reference in its entirety.

TECHNICAL FIELD

The present application relates to personal-care devices, and particularly to such devices for the care of skin.

BACKGROUND

Human skin can be subject to a variety of undesirable conditions, e.g., dandruff, dry flaky skin, or acne. These conditions can be caused by blockage of hair follicles in the skin by cells, dirt and natural oils. Acne can result from an immune response to bacteria growing in plugged follicles. Therefore, it is desirable to reduce such blockages.

Various devices have been developed to assist in the care of skin, e.g., human skin. For example, the SKINFINITY skin-care wand includes a handle with a head. Various skin-care attachments can be mounted on the head, including disposable lotion pads, sponges, or pumice stones. Pumice stones can be used to exfoliate, i.e., to remove dead skin and specifically surface dry skin cells. However, when a person uses a SKINFINITY wand on his own body, the wand places limitations on the areas of the person's body that can be reached, the angles at which they can be reached, and the pressure that can be applied by the user.

U.S. Pat. No. 5,628,083 to Hayes discloses a device including a rigid base panel fastened to a wall using suction cups. Foam is attached to the base panel, and the assembly is covered with a removable cover. A user can attach this device to a shower wall and lean on it or rub against it to clean the user's back. However, suction cups are often unreliable in tile or textured-fiberglass shower or tub surrounds. Moreover, this device can require the user to lean to compensate for the slope of the sides of a bathtub, decreasing comfort and effectiveness.

U.S. Publication No. 2010/0242201 shows various devices that can be used for, e.g., exfoliating the face. However, these devices have very specific sizes for specific applications, e.g., face or leg exfoliation. Multiple, different devices are therefore required to care for respective areas of the body.

U.S. Publication No. 2008/0115302 describes a cleaning tool with a handle and a removable cleaning head. The face of the cleaning head is oriented substantially normal to the long axis of the handle. However, a removable head or the mechanism that selectively retains the head can be susceptible to damage during use, and the tool is limited in where on the body it can reach.

U.S. Publication No. 2011/0197917 by Koptis et al. describes a covering affixable to an apparatus head. The apparatus can dispense flowable solutions. However, this device is limited in the range of areas on the body it can reach.

U.S. Publication No. 20070098768 by Close et al. describes a two-side personal-care appliance. However, this device can only be used on parts of the body a hand can reach.

There is also a need for devices that permit caring for skin under a cast, splint, or other mechanical restraint or brace. WO 99/43249 by Adrian et al. describes an assembly with a substantially flexible elongate body and an abrading surface. The assembly can be, e.g., inserted in a cast from an open end thereof Similarly, U.S. Pat. No. 4,892,091 to Sullenger describes a scratching device with a flexible body, grooves, and hemispherical projections. The ORIGINAL CASTSCRATCHER by ASGO similarly has a flexible elongate body and two differently-shaped ends. However, it can be difficult to control the amount of force applied when using such devices.

U.S. Pat. No. 5,730,709 to Sergent describes a scratching device for a cast. The device includes a length of cord to be pulled within the cast. However, the cord must be positioned in the cast when the cast is first applied, and cannot be removed without either damaging it or rendering it difficult to re-insert.

There is, therefore, a continuing need for improved skin-care devices, both for exposed-skin use and for in-cast use.

BRIEF DESCRIPTION

According to an aspect, there is provided hand-held skin-treatment apparatus, comprising:
 a) a deformable cover enclosing a volume extending in a longitudinal direction, the cover having an exterior surface with a selected surface roughness;
 b) an elongated rigid support member arranged within the volume; and
 c) a compliant member disposed within the volume and at least partly between the support member and the cover, so that the cover is held substantially stationary with respect to the compliant member.

According to another aspect, there is provided hand-held skin-treatment apparatus, comprising:
 a) an elongated flexible support member having dorsal and ventral sides;
 b) a tip protruding transversely from a distal end of the support member;
 c) a handle attached to a proximal end of the support member;
 d) an elongated compliant member attached to the support member along the length of the compliant member; and
 e) a cover enclosing the tip, a portion of the compliant member, and a corresponding portion of the support member;
 f) wherein the cover has lower surface roughness over the dorsal side than over the ventral side.

Various embodiments advantageously provide exfoliation or lotion application that can reduce the severity of undesirable skin conditions without requiring harsh chemicals such as acids. Various aspects advantageously permit users to exfoliate in the shower or bath and apply lotion after a shower. Various aspects advantageously permit caring for skin that is covered or otherwise difficult to access.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 8 is an elevational cross-section of an exemplary skin-treatment apparatus; and FIG. 9 is a plan view of exemplary skin-treatment devices similar to that depicted in FIG. 8.

The attached drawings are for purposes of illustration and are not necessarily to scale.

DETAILED DESCRIPTION

Figure 1:
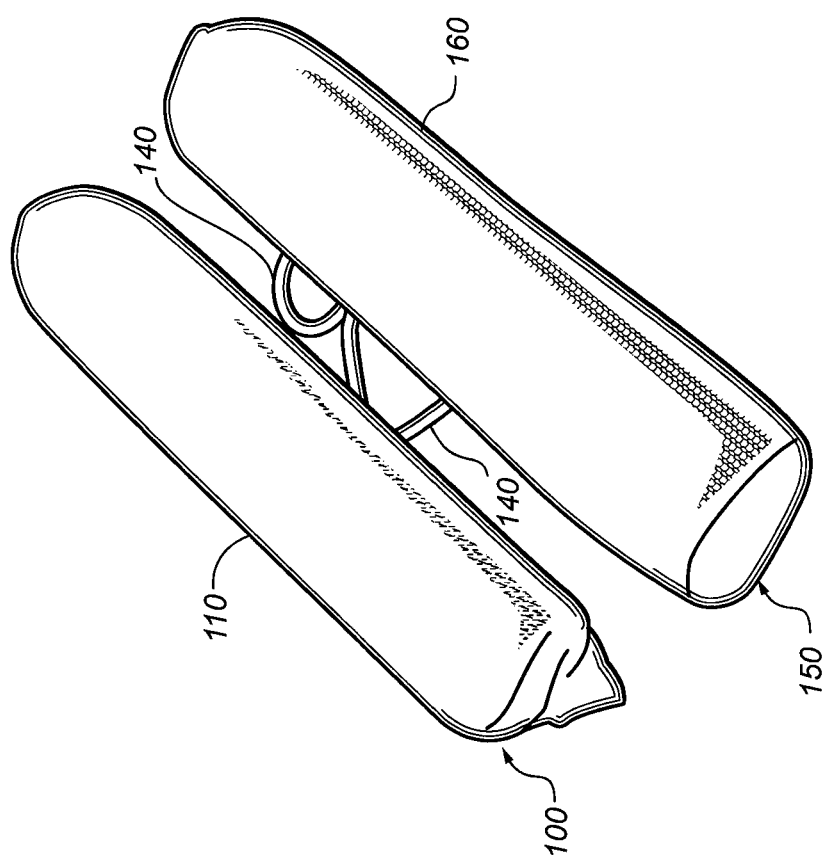
FIG. 1 is a front perspective of skin-treatment apparatus according to various aspects.

FIG. 1 is a front perspective of hand-held skin-treatment apparatus 100, 150 according to various aspects. The examples shown here are in the shape of wands; other shapes can be used. Apparatus 100 can be, e.g., a lotioning wand for applying lotion to hard-to-reach areas of skin, and apparatus 150 can be, e.g., an exfoliating wand for exfoliating hard-to-reach areas of skin. Each apparatus 100, 150 includes a deformable cover 110, 160 enclosing a volume extending in a longitudinal direction. Deformable covers 110, 160 can be, e.g., bendable or stretchable. Covers 110, 160 have respective exterior surfaces (illustrated) with respective, selected surface roughnesses. In this example, cover 160 is rougher than cover 110. Covers 110, 160 can be stitched, e.g., using overlock stitching.

In various aspects, cover 110, 150 includes a nylon mesh that substantially does not retain water. The mesh can, e.g., permit soap suds (water and soap together) to pass through. This can provide the user increased control and a more secure grip. In various aspects, cover 110, 150 can include pores that hold thin soap layers, in much the way that a bubble wand does. These aspects advantageously provide the user enhanced control while applying soap since the soap is not protruding above the pores. In various aspects, cover 110, 150 includes microfleece. Surface tension of the lotion with respect to the fibers of the microfleece can hold lotion on the surface of such a cover.

Various exemplary covers 110, 150 useful with various aspects are (in order from softer to coarser): 100% silk; bamboo charcoal in bamboo fabric; microfleece or other fleece; 60% nylon/40% polyester fabric (for, e.g., soft exfoliation); 25% cotton/75% nylon fabric with embedded bamboo charcoal (for, e.g., moderate exfoliation and detoxification); and 100% nylon (e.g., for stronger exfoliation). Covers 110, 150 including bamboo charcoal can advantageously be colored gray due to the charcoal. This gray color can provide a neutral background, and apparatus 100, 150 having such a neutral background color can be particularly useful for the application of makeup or other colored dermal preparations. Covers 110, 150 can have thicknesses selected according to the mechanical strength of the selected material.

Figure 2:
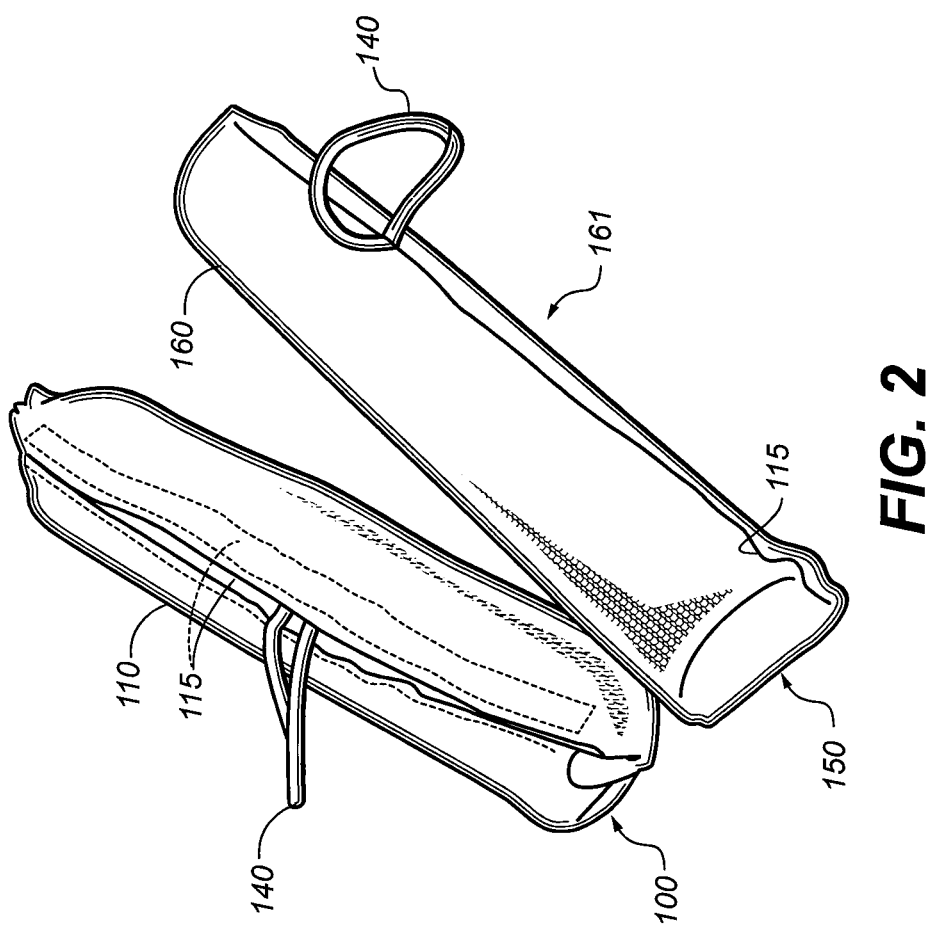
FIG. 2 is a rear perspective of skin-treatment apparatus according to various aspects.

FIG. 2 is a rear perspective of skin-treatment apparatus 100, 150 according to various aspects. Covers 110, 160 are shown. In various aspects, the cross-sectional extent of the volume enclosed by cover 110 or 160 fits in an adult's hand, e.g., in the hand of a $5^{th}$-percentile Japanese female or of a $95^{th}$-percentile American male.

Figure 3:
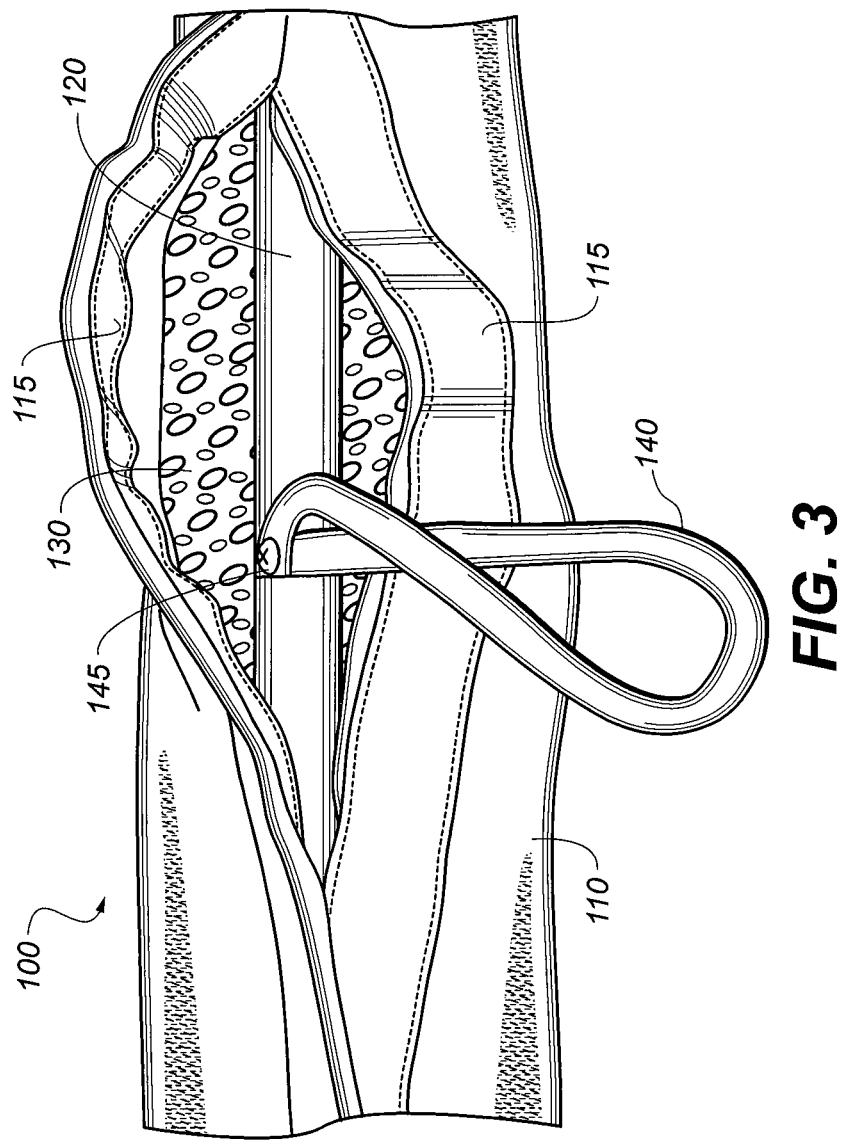
FIGS. 3-6 are perspectives of internal construction of skin-treatment apparatus according to various aspects.

FIG. 3 is a perspective of internal construction of skin-treatment apparatus 100 according to various aspects. Other skin-care devices, e.g., apparatus 150, can have corresponding internal construction.

Elongated rigid support member 120 is arranged within the volume enclosed by cover 110. The term "rigid" includes semirigid supports; it is not required that support member 120 be entirely inflexible. In various aspects, a "rigid" support member 120 is a member stiff enough that radial forces can be transmitted via the support member 120. Support member 120 permits a user to grip the apparatus 100, e.g., near one end, and apply force against the user's body using a non-gripped portion of the apparatus 100, e.g., the other end or the middle. This application of force permits e.g., lotioning or exfoliating. Support member 120 can be surrounded by cover 110, e.g., as shown in FIGS. 1-3. Support member 120 can be formed from a ferrous material, e.g., steel.

Compliant member 130 is disposed within the volume enclosed by cover 110 and is arranged at least partly between the support member 120 and the cover 110. In the view shown, cover 110 wraps around behind support member 120. In an example, compliant member 130 includes polyurethane foam. Compliant member 130 is arranged so that cover 110 is held substantially stationary with respect to compliant member 130. Compliant member 130 may but does not have to fill the volume enclosed by cover 110. Compliant member 130 holds cover 110, e.g., an exfoliator. "Substantially stationary" can permit some shift, e.g., up to ½" or up to ¼", or 2 mm, or 1 mm displacement when used to scrub skin. The permitted shift can be greater when the compliant member is wet and thus softer. Various aspects can be used to apply body wash, which can be a lubricant (e.g., cover 110, FIG. 1). In various aspects, deformable cover 110 can include textiles or can include a material sprayed onto compliant member 130 that can deform with compliant member 130.

In various aspects, apparatus 100 includes handle 140 extending from cover 110. Handles 140 are also shown in FIGS. 1 and 2. Handle 140 can be spaced apart from a longitudinal midpoint 161 (FIG. 2) of the volume enclosed by cover 160 (FIG. 2). The handle 140 can be attached to the support member 120 (as in the example shown), to the compliant member 130, or to cover 110. In various aspects, handle 140 is not a straight handle attached to one end of apparatus 100 or support member 120. The handle 140 can protrude at an angle from the longitudinal axis of support member 120, e.g., substantially perpendicular thereto.

In an example, handle 140 includes or consists of a cord (illustrated) and mounting device 145 to attach the cord to support member 120, compliant member 130, or cover 110. Mounting device 145 can include, e.g., a screw (illustrated), thread, VELCRO, or staples. In various aspects, the mounting device 145 is not presented for the user to grip while using the apparatus (e.g., is under the cover when the apparatus is in normal use). Apparatus 100 (FIG. 2) shows an example of such a configuration; mounting device 145 is contained within cover 110 and handle 140 protrudes therefrom. Apparatus according to various aspects consist of cover 110, support member 120, compliant member 130, and handle 140.

In various aspects, body care wands (apparatus 100, 150) include an antimicrobial cellulose sponge (compliant member 130) and a metal clamp stiffener support bar (support member 120) running lengthwise down the middle of the back of the wand. Covers 110, 160 can be sewn and have hook-and-loop fasteners 115 as closures and a velvet loop (handle 140) to put a hand through or from which to hang the wands, e.g., on a wall-mounted hook.

Cover 110 is an example of a lotioning cover. In an example, cover 110 includes 100-weight or other microfleece. Apparatus 100 with cover 110 can be used, e.g., to apply body lotion after showers and baths. The user can apply the body lotion to the micro fleece wand (apparatus 100) and then use the wand to apply the lotion to the body. Exemplary lotions include OIL OF OLAY, shea butter and shea-butter-containing lotions, and LUBRIDERM THREE-IN-ONE.

Cover 160 is an example of a bath/shower physical exfoliating cover made from, e.g., nylon hydro exfoliating material. Apparatus 150 with cover 160 can be used in the shower/bath to physically exfoliate by scrubbing the skin with wand 150, e.g., after wetting wand 150. Wand 150 can be used in conjunction with body washes.

Any or all of cover 110, hook-and-loop fasteners 115, support member 120, compliant member 130, handle 1040, mounting device 145 can be decorated in a selected color or pattern. For example, cover 110 can be painted, dyed, or silkscreened with the logo or colors of an athletic team or educational institution. In another example, support member 120 can be powder-coated and carry printed matter of a logo of the manufacturer or another party.

Figure 4:
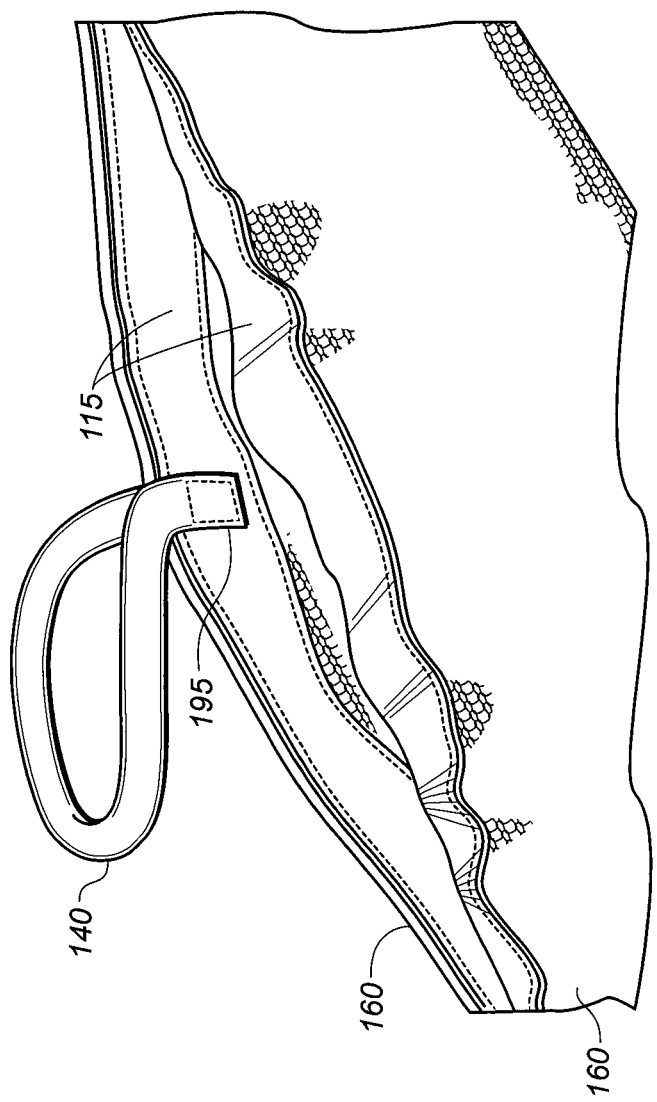

FIG. 4 is a perspective of internal construction of skin-treatment apparatus 100 according to various aspects. Cover 160 includes detachable fastener 115 so that compliant member 130 and support member 120 can be removed from cover 110 when the fastener is detached. In the example shown, fastener 115 includes a hook-and-loop fastener (e.g., a VELCRO strip); a zipper can also or alternatively be used. Fastener 115 is also shown in FIGS. 2 and 3. In those examples, fastener 115 extends down the long axis of apparatus 100. Fastener 115 can also extend along the short axis. For example, cover 110 can be arranged as a tube with one closable end, similar to a sock.

In this example, handle 140 is fastened to cover 160 using mounting device 195. Mounting device 195 includes thread holding handle 140 sewn in to cover 160.

Figure 5:
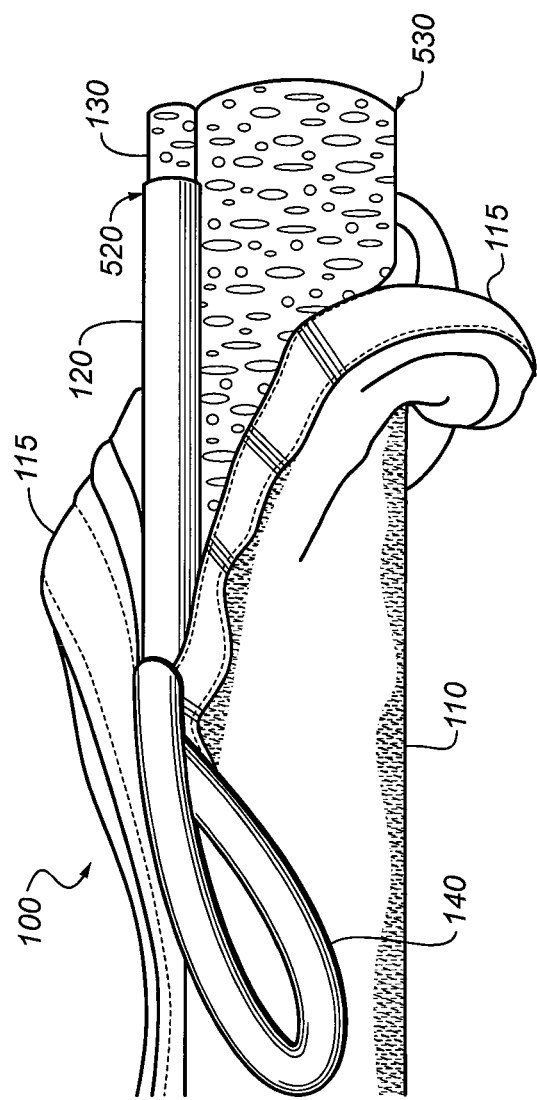

FIG. 5 is a perspective of internal construction of skin-treatment apparatus 100 according to various aspects. Compliant member 130 has two profiled ends (end 530 is shown) corresponding to the longitudinal ends of the support member 120 (end 520) is shown. The profiled ends (e.g., end 530) can be, e.g., chamfered, rounded, or otherwise non-square-edged. In various aspects, the profiled ends are designed and sized to fit in an eye socket to permit care of the skin near the eye. In the example shown, the compliant member 130 protrudes longitudinally (to end 530) beyond the longitudinal ends (e.g., end 520) of support member 120.

Figure 6:
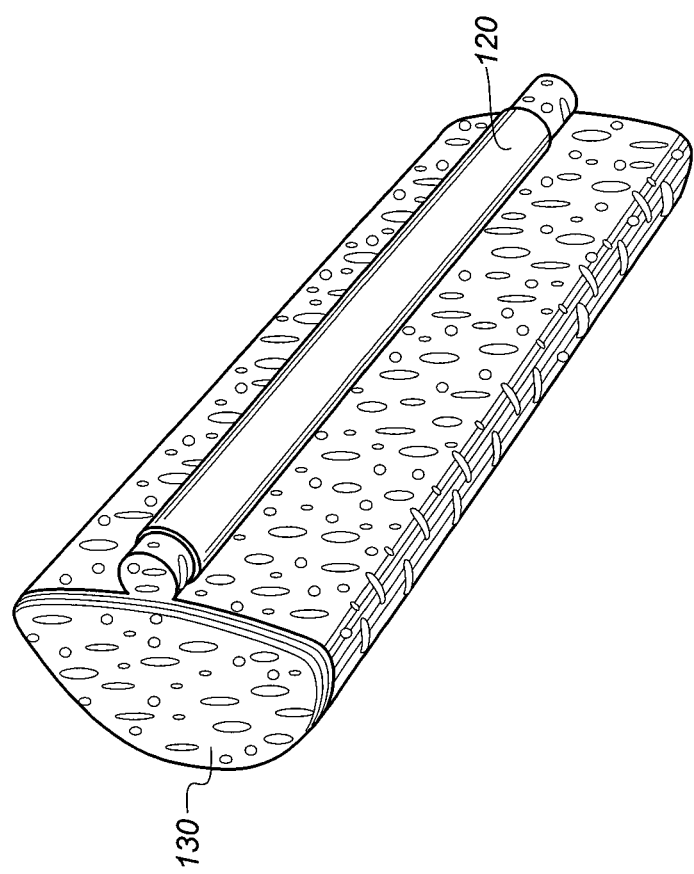

FIG. 6 is a perspective of internal construction of skin-treatment apparatus 100 according to various aspects. In the aspect shown, compliant member 130 extends along at least 90% of the length of support member 120. For example, compliant member 130 can be 13" long and support member 120 can be 12" long. Support member 120 can be or include a stainless steel aluminum clamp. Support member 120 can include a metal tube with a longitudinal slit. The edges of the slit can have teeth or other features to retain compliant member 130. Compliant member 130 can be or include an anti-microbial cellulose sponge. In various aspects, support member 120 can be 6.375" long or 11.75" long.

In various aspects, such as that shown, respective cross-sections of support member 120, compliant member 130, and cover 110 (FIG. 1) are substantially constant along the length of support member 120. In this example, the cross-section can be different at the ends, in the area in which compliant member 130 extends beyond support member 120.

FIGS. 7A-7F depict various configurations of exemplary skin-treatment apparatus. FIGS. 7A-7F are, respectively, end, top, side, bottom, elevational section, and perspective views of an exemplary skin-treatment apparatus.

Figure 7A:
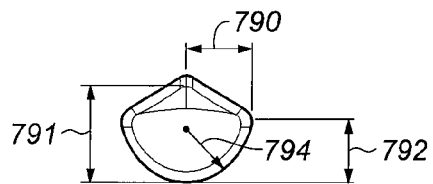
FIGS. 7A-7F are, respectively, end, top, side, bottom, elevational section, and perspective views of an exemplary skin-treatment apparatus.

FIG. 7A is an end view. In an example, dimension 790 can be about 2". Dimension 791 can be about 2.5". Dimension 792 can be about 2". Dimension 794 can be about 1.85".

Figure 7B:
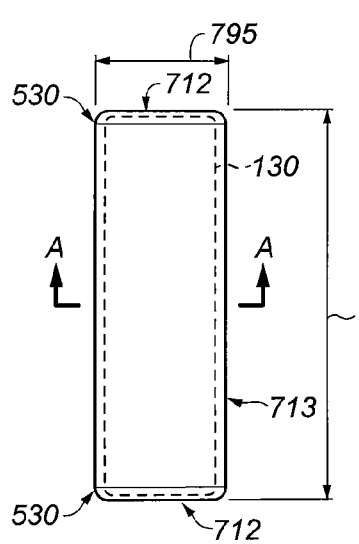

FIG. 7B is a top view. Dimension 795 can be, e.g., about 3.64". Dimension 796 can be, e.g., about 10.3", or about 17". The shape shown is exemplary; various skin-care devices described herein can be tapered, ellipsoidal, American-football-shaped, or other shapes. In at least one aspect, dimension 796 is substantially longer than dimension 795 (or dimension 797, FIG. 7C), e.g., for use as a long, narrow back scratcher. Such aspects can include, e.g., nylon-mesh covers.

In at least one aspect, the volume defined by cover 110 (FIG. 1) is defined at least in part by two substantially parallel ends 712 (which can be profiled ends 530, as discussed above) and a surface 713 connecting the two ends and substantially perpendicular thereto. Cover 110 wraps around the corners or joins between ends 712 and surface 713. The wrap-around portions (e.g., profiled ends 530) can be used for exfoliating or lotioning small areas of skin or tight spaces. Ends 712 or surface 713 can be used for care of larger areas of skin. Various aspects advantageously permit caring for both large and small areas of skin using a single skin-care apparatus.

In various aspects, cover 110 can expose a selected surface over substantially all the apparatus. Cover 110 can expose the selected surface over two longitudinal ends 712 of the apparatus. The apparatus can be arranged so no portion of the apparatus extends beyond cover 110.

Figure 7C:
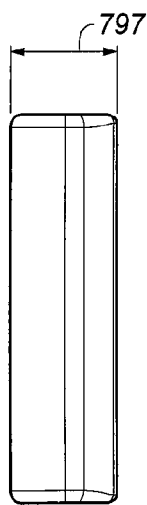

FIG. 7C is a side view. Dimension 797 can be, e.g., about 2.76".

Figure 7D:
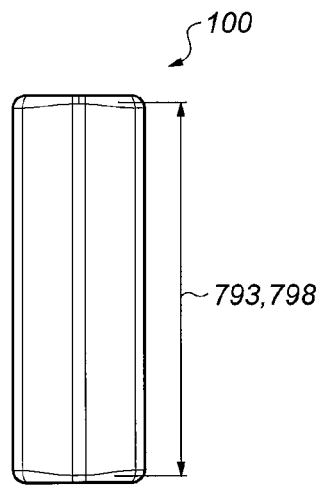

FIG. 7D is a back view. Dimensions 793, 798 can be, e.g., about 10", or about 6", or about 13", or about 15.1".

Figure 7E:
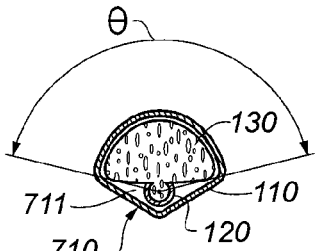

FIG. 7E is an elevational cross-section along the line A-A in FIG. 7B. Cover 110, support member 120, and compliant member 130 are as shown in FIG. 5. Volume 711 is enclosed by cover 110.

In various aspects, compliant member 130 subtends an angle θ azimuthally, i.e., around the longitudinal axis of support member 120. In an exemplary aspect, compliant member 130 extends azimuthally at least one quarter of the way around support member 120. An example of such an extent is shown in FIG. 7E. As can be seen, the illustrated angle θ is over 150°.

In various aspects, compliant member 130 protrudes radially at least 10 mm from support member 120. This permits compliant member 130 to mold to the shape of the user's body.

Figure 7F:
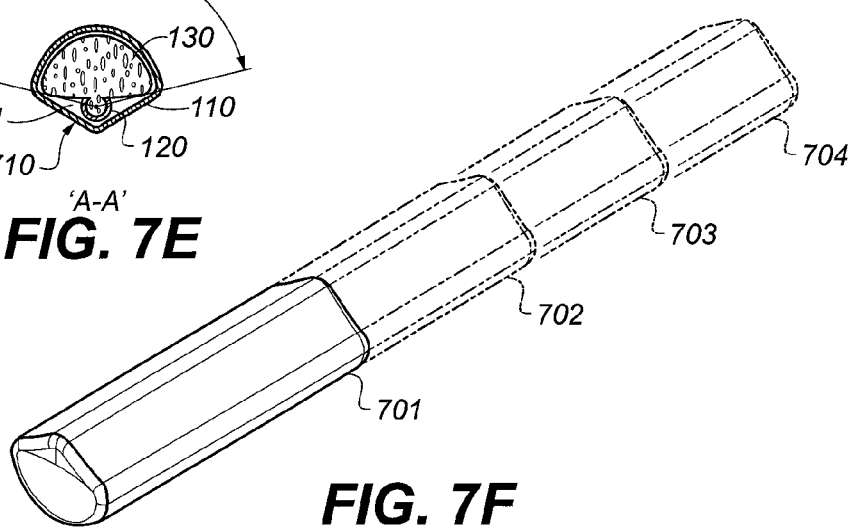

FIG. 7F is a perspective showing apparatus 701, e.g., about 6" long. FIG. 7F also shows, in phantom, apparatus 702, 703, 704, having lengths of about 10", about 13", and about 15" respectively. Widths can be, e.g., from 2" to 3.5"; heights can be, e.g., from 2" to 2.75". In various aspects, support member 120 is at least three times as long as a largest width of compliant member 130, or at least four, ten, or fifteen times as long.

In various aspects, a skin-care apparatus as described herein is arranged so that handle 140 (FIGS. 3, 4) includes a cord and a mounting device (e.g., device 145 or 195) to attach the cord to support member 120, compliant member 130, or cover 110 (all FIG. 3). Compliant member 130 extends along at least 90% of the length of support member 120 (as shown in, e.g., FIG. 6). Compliant member 130 extends azimuthally at least one quarter of the way around support member 120, e.g., as noted above with reference to FIG. 7E.

Two exemplary skin-care wands were constructed. One wand corresponded to apparatus 150 (FIG. 1) and had a nylon mesh cover 160. This wand is useful for, e.g., exfoliating. The other constructed wand corresponded to apparatus 100 (FIG. 1). This wand had a microfleece cover 110 and is useful for, e.g., applying lotion. Each apparatus 100, 150 has a cover 110, 160 that fastens closed around the compliant member 130 and support member 120 using a hook-and-loop fastener 115 (e.g., VELCRO). The compliant member 130 and support member 120 were assembled together, e.g., similarly to a foam mop head. Each apparatus 100, 150 has a handle 140 including a loop of cord, e.g., velvet cord. Compliant members 130 are formed from antibacterial foam and support members 120 are formed from split metal tubing crimped around a portion of the foam of compliant member 130. These and other aspects can be useful for caring for skin, e.g., for applying lotion to dry skin, e.g., without smearing it, or to increasing blood flow in areas of skin such as scar tissue by exfoliating those areas.

FIGS. 1-7F illustrate various aspects, including hand-held wands for care of exposed skin, e.g., while bathing. In various aspects, the described components are arranged slimmer and longer to permit, e.g., scratching back itches without harming the skin of the back. Wands described herein, whether for bathing or for back-scratching, can include handles 140, or not. However, there is a further need for ways of caring for non-exposed skin. Examples of non-exposed skin include skin covered by a cast during a user's recovery from a broken bone and skin under pads of a sports or military uniform.

FIG. 8 is an elevational cross-section of an exemplary skin-treatment apparatus. FIG. 9 is a plan view of exemplary skin-treatment devices similar to that depicted in FIG. 8. The illustrated apparatus can be used for various purposes, including but not limited to scratching itches inside of body casts without harming the skin.

Such apparatus can be, e.g., a scratcher for scratching under a cast or under sports equipment when waiting between periods without changing clothes. In this aspect, hand-held skin-treatment apparatus can include an elongated flexible support member 820 having dorsal and ventral sides 821, 822 respectively. Support member 820 can include 1/16" thick SS[ ]. Ventral side 822 can be oriented toward the body of the person or subject being scratched. Support member 820 can be, e.g., sufficiently flexible to travel between a cast or protective pad and the body of a person or subject. In the example shown, support member 820 supports handle 805 and head 850, which includes compliant member 830 and cover 810.

A tip 840 can protrude transversely from a distal end of the support member 820. Tip 840 can protrudes from the distal end of support member 820 in both dorsal and ventral directions, or in only one of those directions. Tip 840 can extend, e.g., ¾" normal to the long axis of support member 820 (up and down in FIG. 8). A handle 805 can be attached to a proximal end of the support member 820. Head 850 can be, e.g., ½" thick (up and down in FIG. 8) between tip 840 and handle 805. An elongated compliant member 830 can be attached to the support member 820 along the length of the support member 820.

A cover 810 can enclose the tip 840, a portion (e.g., part or all) of the compliant member 830, and a corresponding portion of the support member 820. The cover 810 can have lower surface roughness over the dorsal side 821 than over the ventral side 822. This is graphically represented in FIG. 8 by the peaked appearance of cover 810 over ventral side 822 and the smooth appearance of cover 810 over dorsal side 821. In various aspects, cover 810 includes silk over the dorsal side 821. Cover 810 can include, e.g., 100% silk material over the ventral side 822 and nylon hydro exfoliating material over the dorsal side 821, e.g., for exfoliating or for scratching itches. Cover 810 can include, e.g., 100% silk material over the ventral side 822 and 100 microfleece over the dorsal side 821, e.g., for lotioning. Other configurations of covers described above can also be used.

The handle 805 or compliant member 830 can each fully enclose the support member 820, or abut it or each other. In various aspects, cover 810 encloses all of the compliant member 830 and encloses that portion of the support member 820 not enclosed by or in contact with the handle 805. The support member 820 and the handle 805 can be collinear, e.g., there can be no bend angle between support member 820 and handle 805. The handle 805 can nest inside the support member 820, or the support member 820 can nest inside the handle 805, or neither can nest inside the other.

In various aspects, compliant member 830 includes hypoallergenic open-cell foam molded onto support member 820. The foam can have a thickness of between ⅛" and ¼". Support member 820 includes a flat flexible stainless steel core with holes punched or otherwise formed therein to permit the molded foam to more effectively adhere to the stainless steel. The open cell hypoallergenic foam can run the length of the apparatus with the exception of handle 805 and can be molded onto the SS[ ] core.

Tip 840 can be shaped to permit more effective scratching action and to slide easily over the inner fabric wrap of casts. In the example shown, tip 840 has a diamond shape. Tip 840 can have rounded corners or a combination of rounded and sharp corners. The exemplary tip shape shown keeps support member 820 away from either the cast or the skin. This reduces the probability that support member 820 will snag on a cast or other covering. This tip shape also reduces the probability that support member 820 will poke the user. Moreover, the exemplary tip shape and related shapes increase the force applied between tip 840 and the user's skin without requiring the user to apply more force in the up-and-down direction of the figure, in which direction support member 820 is flexible. The illustrated tip shape and similar tip shapes thus advantageously permit users to effectively care for their skin without concern for damage to any coverings of the skin. Such tip shapes provide, e.g., more effective exfoliation by making use of the narrowness of the space in which they are used to provide higher forces between the tip and the skin.

FIG. 9 shows a top view of apparatus such as that described above with reference to FIG. 8. Handle 920, head 910, and tip 940 are shown. Three lengths are shown in phantom. Apparatus such as described above can be long and slender, e.g., having lengths of 12" (solid; e.g., with a 6" long head 910), 18" (phantom; e.g., with a 12" long head 910), 24" (phantom; e.g., with an 18" long head 910) and 36" (phantom; e.g., with a 30" long head 910). Handle 920 can be 4"-5" long and can be made from rubber, wood, plastic, or stainless steel. Handle 920 can be covered with a rubber handle cover. Handle 920 can include a velvet hang-up tie placed through a hole (shown) in handle 920. Handle 920 can be, e.g., about 1.1875" wide.

Various aspects advantageously permit users to more effectively care for their skin or mitigate common skin conditions. For example, blemished skin can be caused by drying out the skin with chemical acne products. Some of these products tend to dry out the skin, and this can result in not only irritated skin but also in future breakouts due to surface dry skin cell buildup. The dry skin cells act as a barrier to trap oil in the skin, thereby starting a cycle of new breakouts. In another example, post-breakout red/dark marks can also benefit from exfoliation, e.g., using apparatus 150 (FIG. 1). Red, dark marks can remain on the skin long after a breakout has healed. The more a user removes the surface damaged skin tissue via exfoliation, the more of the dark marks are removed and the more the formation of new healthy (non-scarred) skin tissue is encouraged. This can advantageously provide more even-toned skin with less scarring as well as fading of stubborn acne scars.

In yet another example, exfoliation can mitigate clogging of pores. Clogged pores are not infected blemishes, but rather blackheads, small whiteheads, and small clogged bumps on the skin, often on the forehead. As with blemished skin, the more the user removes surface dry skin cells (usually caused by using harsh, drying products), the less oil will stay trapped and congested in the pores to cause clogging.

In still another example hyper-pigmentation can be mitigated by exfoliation, e.g., using apparatus 150. Hyper-pigmentation is the appearance of brown spots on the skin as a result of, e.g., age, pregnancy, hormonal changes, or genetics. These spots tend to become more apparent and darker as the skin ages. Exfoliation can advantageously break up or otherwise disrupt the pigmented cells to allow them to fade.

In a further example, lotioning, e.g., using apparatus 100 (FIG. 1) can mitigate dry skin. Users can exfoliate to remove dry skin cells and lotion to moisturize new skin cells, resulting in a moister skin.

Accordingly, various aspects permit reducing pimples, acne, dry skin, hyper pigmentation, rough skin, or dandruff without the use of chemicals. Various aspects advantageously benefit skin conditions such as psoriasis. Apparatus according to various aspects permit effectively exfoliating and lotioning the entire body. Apparatus described herein permits readily accessing "hard to reach" areas of the body such as the back. When used regularly, skin-care wands described herein can provide improved skin, hair and overall appearance.

Various examples of elongated skin-care apparatus such as those shown in FIGS. 8 and 9 advantageously permit obtaining the above-described advantages and benefits even with respect to skin that is covered or difficult to access, e.g., skin on a limb surrounded by a cast. These aspects can also provide skin care underneath clothing or other skin coverings.

Various aspects of skin-care apparatus described herein can be disposable or partly disposable, e.g., can include disposable covers. Various aspects herein can be usable by, e.g., adults, children, or caretakers (of, e.g., children, the ill, or the elderly).

Various aspects are described herein; this disclosure includes combinations of the described aspects. The invention is inclusive of combinations of the aspects described herein. References to "a particular aspect" (or "embodiment" or "version") and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A hand-held skin-treatment apparatus, comprising:
   a) a deformable cover enclosing a volume extending in a longitudinal direction, the cover having an exterior surface with a selected surface roughness;
   b) an elongated rigid support member defined by a substantially cylindrical configuration arranged within the volume of the deformable cover; and
   c) a compliant member arranged within the volume of the deformable cover and at least partly between the support member and the cover, so that the cover is held substantially stationary with respect to the compliant member, the compliant member having opposing end surfaces and a flat side between the opposing end surfaces, and the rigid elongated support member is attached to the flat side, the support member having opposed ends that are supported along the longitudinal direction by profiled ends formed on the flat side of the compliant member and in which the compliant member extends azimuthally a portion around the elongated rigid support member, the deformable cover entirely surrounding the compliant member and the elongated rigid support member.

2. The apparatus according to claim 1, further including a handle extending from the cover and spaced apart from a longitudinal midpoint of the volume.

3. The apparatus according to claim 2, wherein the handle consists of a cord and a mounting device to attach the cord to the support member, the compliant member, or the cover.

4. The apparatus according to claim 2, consisting of the cover, the support member, the compliant member, and the handle.

5. The apparatus according to claim 4, wherein:
   a) the handle includes a cord and a mounting device to attach the cord to the support member, the compliant member, or the cover;
   b) the compliant member extends along at least 90% of the length of the support member; and
   c) the compliant member extends azimuthally at least one quarter of the way around the support member.

6. The apparatus according to claim 1, wherein the cross-sectional extent of the volume fits in an adult's hand.

7. The apparatus according to claim 1, wherein respective cross-sections of the support member, the compliant member, and the cover are substantially constant along the length of the support member.

8. The apparatus according to claim 1, wherein the compliant member extends along at least 90% of the length of the support member.

9. The apparatus according to claim 1, wherein the compliant member protrudes longitudinally beyond the longitudinal ends of the support member.

10. The apparatus according to claim 1, wherein the compliant member extends azimuthally at least one quarter of the way around the outer circumference of the support member.

11. The apparatus according to claim 1, wherein the compliant member protrudes radially at least 10 mm from the support member.

12. The apparatus according to claim 1, wherein the cover includes a nylon mesh that substantially does not retain water.

13. The apparatus according to claim 1, wherein the cover includes microfleece.

14. The apparatus according to claim 13, wherein the cover is configured to receive lotion to apply to the body.

15. The apparatus according to claim 1, wherein the cover includes a detachable fastener, so that the compliant member and the support member can be removed from the cover when the fastener is detached.

16. The apparatus according to claim 15, wherein the detachable fastener is one of hook and loop fasteners or a zipper.

17. The apparatus according to claim 1, wherein the support member is at least three times as long as a largest width of the compliant member.

18. The apparatus according to claim 1, wherein the volume is defined at least in part by two substantially parallel ends and a surface connecting the two ends and substantially perpendicular thereto.

19. The apparatus according to claim 1, wherein the profiled ends are sized to fit in an eye socket to permit care of the skin near the eye.

20. The apparatus according to claim 1, wherein the apparatus is used for exfoliating.

\* \* \* \* \*